United States Patent
Zhang et al.

(10) Patent No.: US 11,280,727 B2
(45) Date of Patent: Mar. 22, 2022

(54) DEPTH-RESOLVED MID-INFRARED PHOTOTHERMAL IMAGING OF LIVING CELLS AND ORGANISMS WITH SUB-MICRON SPATIAL RESOLUTION

(71) Applicant: PURDUE RESEARCH FOUNDATION, West Lafayette, IN (US)

(72) Inventors: Delong Zhang, Brighton, MA (US); Ji-Xin Cheng, Newton, MA (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 15/715,534

(22) Filed: Sep. 26, 2017

(65) Prior Publication Data
US 2018/0088041 A1    Mar. 29, 2018

Related U.S. Application Data

(60) Provisional application No. 62/400,582, filed on Sep. 27, 2016.

(51) Int. Cl.
*G01N 21/35* (2014.01)
*G01N 21/17* (2006.01)
(Continued)

(52) U.S. Cl.
CPC .......... *G01N 21/3563* (2013.01); *C12Q 1/02* (2013.01); *G01J 5/22* (2013.01); *G01N 21/171* (2013.01);
(Continued)

(58) Field of Classification Search
CPC ......... G01N 21/171; G01N 2021/1725; G01N 2021/1712; G01N 2021/1714;
(Continued)

(56) References Cited

U.S. PATENT DOCUMENTS 2,940,355 A    6/1960   Cary
5,574,562 A    11/1996  Fishman et al.
(Continued)

FOREIGN PATENT DOCUMENTS

CN    105699358 A      6/2016
DE    102014108424 B3  6/2015
(Continued)

OTHER PUBLICATIONS

Article "Helium-Neon Laser," University of New Mexico, dated Nov. 22, 2012 (Retrieved on May 4, 2018), 6 pages.
(Continued)

*Primary Examiner* — Mark R Gaworecki

(74) *Attorney, Agent, or Firm* — Patterson Thuente Pedersen, P.A.

(57) ABSTRACT

Systems and methods for sensing vibrational absorption induced photothermal effect via a visible light source. A Mid-infrared photothermal probe (MI-PTP, or MIP) approach achieves 10 mM detection sensitivity and sub-micron lateral spatial resolution. Such performance exceeds the diffraction limit of infrared microscopy and allows label-free three-dimensional chemical imaging of live cells and organisms. Distributions of endogenous lipid and exogenous drug inside single cells can be visualized. MIP imaging technology may enable applications from monitoring metabolic activities to high-resolution mapping of drug molecules in living systems, which are beyond the reach of current infrared microscopy.

31 Claims, 8 Drawing Sheets

(51) Int. Cl.

| | |
|---|---|
| *C12Q 1/02* | (2006.01) |
| *G01J 5/22* | (2006.01) |
| *G01N 21/3563* | (2014.01) |
| *G01J 5/00* | (2022.01) |
| *G02B 21/02* | (2006.01) |
| *G02B 21/06* | (2006.01) |
| *G02B 21/18* | (2006.01) |
| *H01S 5/34* | (2006.01) |

(52) U.S. Cl.
CPC ............... *G01J 2005/0077* (2013.01); *G01N 2021/1712* (2013.01); *G01N 2201/0612* (2013.01); *G01N 2201/0697* (2013.01); *G02B 21/02* (2013.01); *G02B 21/06* (2013.01); *G02B 21/18* (2013.01); *H01S 5/3401* (2013.01)

(58) Field of Classification Search
CPC ....... G01N 21/3563; G01N 2201/0612; G01N 2201/0697; C12Q 1/02; G01J 5/22; G01J 2005/0077; G02B 21/02; G02B 21/06; G02B 21/18; H01S 5/3401
See application file for complete search history.

(56) References Cited

U.S. PATENT DOCUMENTS

| | | | |
|---|---|---|---|
| 6,532,070 | B1 | 3/2003 | Hovinen et al. |
| 7,630,081 | B2 | 12/2009 | Ressler et al. |
| 7,855,780 | B1 | 12/2010 | Djeu |
| 8,001,830 | B2 | 8/2011 | Dazzi et al. |
| 8,242,448 | B2 | 8/2012 | Prater et al. |
| 8,402,819 | B2 | 3/2013 | Dazzi et al. |
| 8,607,622 | B2 | 12/2013 | Dazzi et al. |
| 8,646,319 | B2 | 2/2014 | Prater et al. |
| 8,680,457 | B2 | 3/2014 | Maxik et al. |
| 8,793,811 | B1 | 7/2014 | Prater et al. |
| 8,869,602 | B2 | 10/2014 | Belkin et al. |
| 9,046,492 | B1 | 6/2015 | Prater |
| 9,091,594 | B2 | 7/2015 | Furstenberg et al. |
| 9,134,341 | B2 | 9/2015 | Prater et al. |
| 9,250,061 | B2 | 2/2016 | Lorbeer et al. |
| 9,372,154 | B2 | 6/2016 | Prater |
| 9,658,247 | B2 | 5/2017 | Yang et al. |
| 9,841,324 | B2 | 12/2017 | Furstenberg et al. |
| 10,228,388 | B2 | 3/2019 | Prater et al. |
| 10,228,389 | B2 | 3/2019 | Yang et al. |
| 10,241,131 | B2 | 3/2019 | Prater |
| 10,473,693 | B2 | 11/2019 | Yang et al. |
| 10,677,722 | B2 | 6/2020 | Li et al. |
| 10,696,405 | B2 | 6/2020 | Dowty et al. |
| 10,845,248 | B1 | 11/2020 | Cheng et al. |
| 10,942,116 | B2 | 3/2021 | Prater et al. |
| 2002/0105641 | A1 | 8/2002 | Anderson |
| 2004/0085540 | A1 | 5/2004 | Lapotko et al. |
| 2004/0188602 | A1 | 9/2004 | Chinn et al. |
| 2005/0105099 | A1 | 5/2005 | Shpantzer et al. |
| 2008/0304046 | A1 | 12/2008 | Lee et al. |
| 2009/0161092 | A1 | 6/2009 | Zanni et al. |
| 2009/0236528 | A1 | 9/2009 | Shpantzer et al. |
| 2009/0249521 | A1 | 10/2009 | Dazzi et al. |
| 2010/0044570 | A1 | 2/2010 | McGill et al. |
| 2010/0079842 | A1 | 4/2010 | Dunleavy et al. |
| 2010/0315646 | A1* | 12/2010 | Chism, II ............... G01N 21/55 356/445 |
| 2010/0320171 | A1 | 12/2010 | Mao et al. |
| 2011/0122488 | A1 | 5/2011 | Truong et al. |
| 2011/0248166 | A1 | 10/2011 | Diem et al. |
| 2012/0002030 | A1 | 1/2012 | Kalkbrenner et al. |
| 2012/0026485 | A1* | 2/2012 | Couston ............... G01N 21/171 356/125 |
| 2012/0122084 | A1 | 5/2012 | Wagner et al. |
| 2012/0167261 | A1 | 6/2012 | Belkin et al. |
| 2012/0314206 | A1 | 12/2012 | Spizig et al. |
| 2013/0134310 | A1 | 5/2013 | Furstenberg et al. |
| 2013/0162994 | A1* | 6/2013 | Xie ............... G01N 21/171 356/342 |
| 2014/0009808 | A1 | 1/2014 | Wang et al. |
| 2014/0289912 | A1 | 9/2014 | Andreev |
| 2014/0361150 | A1* | 12/2014 | Cheng ............... G02B 21/002 250/214 A |
| 2015/0085098 | A1 | 3/2015 | Dowaki et al. |
| 2015/0219684 | A1 | 8/2015 | Humphris et al. |
| 2015/0285836 | A1 | 10/2015 | Humphris et al. |
| 2015/0308947 | A1 | 10/2015 | Xu et al. |
| 2016/0011049 | A1 | 1/2016 | Furstenberg et al. |
| 2016/0161245 | A1 | 6/2016 | Fu et al. |
| 2017/0127983 | A1 | 5/2017 | Spegazzini et al. |
| 2017/0146455 | A1 | 5/2017 | Mantele et al. |
| 2018/0007343 | A1 | 1/2018 | Send et al. |
| 2018/0052186 | A1 | 2/2018 | Su et al. |
| 2018/0156674 | A1 | 6/2018 | Fleming et al. |
| 2018/0180642 | A1 | 6/2018 | Shetty et al. |
| 2018/0246032 | A1* | 8/2018 | Li ............... G01N 21/3563 |
| 2018/0259553 | A1 | 9/2018 | Yang et al. |
| 2018/0364158 | A1 | 12/2018 | Wang et al. |
| 2019/0120753 | A1 | 4/2019 | Prater et al. |
| 2019/0204230 | A1 | 7/2019 | Ota |
| 2019/0317012 | A1 | 10/2019 | Furstenberg et al. |
| 2020/0025677 | A1 | 1/2020 | Prater et al. |
| 2020/0217643 | A1 | 7/2020 | Schnell et al. |
| 2020/0378829 | A1 | 12/2020 | Schnell et al. |
| 2021/0003504 | A1 | 1/2021 | Li et al. |

FOREIGN PATENT DOCUMENTS

| | | |
|---|---|---|
| WO | WO 2013/078471 A1 | 5/2013 |
| WO | WO 2018/102467 A1 | 6/2018 |

OTHER PUBLICATIONS

Bialkowski, "Application of the BaTiO3 Beam-Fanning Optical Limiter as an Adaptive Spatial Filter for Signal Enhancement in Pulsed Infrared Laser-Excited Photothermal Spectroscopy," Optics Letters, Sep. 1989, 3 pages.

Bialkowski, "Pulsed-Laser Excited Differential Photothermal Deflection Spectroscopy," Society for Applied Spectroscopy, 1992, 11 pages.

Bialkowski, "Ultrasensitive Photothermal Deflection Spectrometry Using an Analyzer Etalon," American Chemical Society, 1988, 6 pages.

Boyer et al., "Photothermal Imaging of Nanometer-Sized Metal Particles Among Scatters," Science, vol. 297, Aug. 2002, 4 pages.

Brandstetter et al., "High Power Terahertz Quantum Cascade Lasers with Symmetric Wafer Bonded Active Regions," Applied Physics Letters 103, 171113 (2013), 6 pages.

Burghoff et al., "Terahertz Laser Frequency Combs," Nature Photonics, 2014, 10 pages.

Cariou et al., "Refractive-Index Variations with Temperature of PMMA and Polycarbonate," Applied Optics vol. 25, No. 3, 1986.

Dowrey et al., Industrial Applications of Near-IR Imaging, Spectrochemical Analysis Using Infrared Multichannel Detectors, Blackwell Publishing, 2005, pp. 175-188.

Gorgulu et al. "All-Silicon Ultra-Broadband Infrared Light Absorbers," Scientific Reports, 2016, 7 pages.

Grodecki et al., "Optical Absorption and Raman Scattering Studies of FewLayer Epitaxial Graphene Grown on 4H—SiC Substrates," Acta Phys. Pol. A 116.5 (2009); 835-837 (Year 2009).

Harthcock et al., Applications of Transmittance and Reflectance Micro/FT-IR to Polymeric Materials, Analytical Services, vol. 40, Issue 2, 1986, pp. 210-214.

Harthcock et al., Imaging with Functional Group Maps Using Infrared Microspectroscopy, Analytical and Engineering Sciences, vol. 42, Issue 3, 1988, pp. 449-455.

Hemming et al., "A High Power Mid-IR ZGP Ring OPO," with over 30 W of optical power (DOI: 10.1364/CLEO_SI.2013.CW1B.7).

Inoue et al., "Realization of Dynamic Thermal Emission Control," Kyoto University, Jul. 2014, pp. 928-931.

(56) References Cited

OTHER PUBLICATIONS

Jiang et al., "Compact High Power Mid-Infrared Optical Parametric Oscillator Pumped by a Gain-Switched Fiber Laser with Figure-of-h Pulse Shape," Optical Society of America, 2015, 6 pages.
Jiang et al., "Narrow-Linewidth Megahertz-Repetition-Rate Optical Parametric Oscillator for High-Speed Flow and Combustion Diagnostics", Applied Optics, vol. 47, No. 1, 2008, pp. 64-71.
Jung et al., "Infrared Broadband Metasurface Absorber for Reducing the Thermal Mass of a Microbolometer," Scientific Reports, 2017, 8 pages.
Kluk et al., "A High-Bandwidth, High-Precision, Two-Axis Steering Mirror with Moving Iron Actuator," Mechanical Engineering Department, Massachusetts Institute of Technology, 2010, pp. 552-557.
Li et al., "Super-Resolution Imaging with Mid-IR Photothermal Microscopy on the Single Particle Level," SPIF Proceedings vol. 9549, 954912-1, 2015, 8 pages.
Liu, "Differential Interference Contrast-Photothermal Microscopy in Nanospace: Impacts of Systematic Parameters," Journal of Microscopy, Mar. 2017, 9 pages.
Marcott et al., "Mining the Information Content Buried in Infrared and Near-Infrared Band Shapes by Temporal, Spatial, and Other Perturbations," Applied Spectroscopy, 2009, 9 pages.
Moscatelli, "Tiny Lenses for Miniature Devices," Scientific American, Dec. 2019, 1 page.
Peng et al., High-Power Mid-Infrared Tunable Optical Parametric Oscillator Based on 3-mm-Thick PPMgCLN[1], Institute of Applied Electronics, China Academy of Engineering Physics, 2012, pp. 87-90.
Selmke et al., "Photothermal Single Particle Microscopy: Detection of a Nanolens," ACS Nano, 2011, 11 pages.
Sullenberger et al., "Spatially-Resolved Individual Particle Spectroscopy Using Photothermal Modulation of Mie Scattering," Massachusetts Institute of Technology, vol. 42, No. 2, Jan. 15, 2017, pp. 203-206.
Tapos et al., "High Bandwidith Fast Steering Mirror," Optomechanics, 2005, 14 gages.
Wang et al., "High-Power Terahertz Quantum Cascade Lasers with ~0.23 W in Continuous Wave Mode," AIP Advances, 2016, 6 pages.
Webpage—Optotronics—https://www.optotronics.com/532nm-green-laser-systems.php, 2017, 2 pages.
Zanuto, "Analysis of the TherIno-Reflectivity Coefficient Influence Using Photothennal Pump-Probe Techniques," Applied Spectroscopoy, 2016, 7 pages.
Zhao, "Heterogeneous and Cross-Distributed Metal Structure Hybridized with Mos2 as High-Performance Flexible SERS Substrate," School of Physics and Electronics, Sep. 2018, 13 pages.
Application and file history for U.S. Appl. No. 15/826,147, filed Nov. 29, 2017. Inventors: Shetty et al.
Application and file history for U.S. Appl. No. 15/917,210, filed Mar. 9, 2018. Inventors: Yang et al.
Application and file history for U.S. Appl. No. 16/155,089, filed Oct. 9, 2018. Inventors: Prater et al.
Application and file history for U.S. Appl. No. 16/465,824, filed May 31, 2019. Inventors: Prater et al.
Callaway, "It Opens up a Whole New Universe: Revolutionary Microscopy Technique See Individual Atoms for First Time," Nature, vol. 582, Jun. 11, 2020, 2 pages.

Cho Pak et al., "Investigation of Standoff Explosives Detection Via Photothermal/Photoacoustic Interferometry," Chemical, Biological, Radiological, Nuclear, and Explosives Sensing XII, vol. 8018, No. 1, May 13, 2011, 15 pages.
Totachawattana et al. "Optimization of Mid-IR Photothermal Imaging for Tissue Analysis," Visual Communications and Image Processing, Aug. 26, 2015, 7 pages.
Nedosekin et al., "Photothermal Confocal Spectromicroscopy of Multiple Cellular Chromophores and Fluorophores," Biophysical Journal, Feb. 1, 2012, 10 pages.
Zhang et al., "Depth-Resolved Mid-Infrared Photothermal Imaging of Living Cells and Organisms with Submicrometer Spatial Resolution," Science Advances, Sep. 28, 2016, 8 pages.
PCT Application No. PCT/US2017/053407, Search Report and Written Opinion dated Dec. 1, 2017, 12 pages.
Article "Photothermal Lens Technique—Theory and Instrumentation," Swofford, 2015, 42 pages.
Fournier et al., "Tomographic Approach for Photothermal Imaging Using the Mirage Effect," Journal of Physique Collogues, 1983, pp. C6-479-C6-482.
Furstenberg et al., "Chemical Imaging Using Infrared Photo— Thermal Microspectroscopy," U.S. Naval Research Laboratory, 2012, 10 pages.
Gaiduk et al., "Room-Temperature Detection of a Single Molecule's Absorption by Photothermal Contrast," Science, 2010, 4 pages.
Harada et al., "Photothermal Microscopy with Excitation and Probe Beams Coaxial Under the Microscope and Its Application to Microparticle Analysis," 1993, 2938-2940.
Lasne et al., "Label-Free Optical Imaging of Mitochondria in Live Cells," Optical Society of America, 2007, 10 pages.
Li et al., "Mid-Infrared Photothermal Imaging of Active Pharmaceutical Ingredients at Submicrometer Spatial Resolution," Anal. Chem., 89, 2017, 4863-4867.
Li et al., "Super-Resolution Far-Field Infrared Imaging by Photothermal Heterodyne Imaging," The Journal of Physical Chemistry B, 2017, 8838-8846.
Li et al., "Super-Resolution Mid-Infrared Imaging Using Photothermal Microscopy," Conference on Lasers and Electro-Optics, Optical Society of America, San Jose, California 2016, p. ATu3J7.
Mertiri et al., "Label Free Mid-IR Photothermal Imaging of Bird Brain with Quantum Cascade Laser," CLEO: Applications and Technology, Optical Society of America, 2014, p. AF1B4.
Mertiri et al., "Nonlinear Midinfrared Photothermal Spectroscopy Using Zharov Splitting and Quantum Cascade Lasers," Jul. 18, 2014, ACS Photonics, vol. 1, pp. 696-702.
Mertiri et al., "Mid-Infrared Photothermal Heterodyne Spectroscopy in a Liquid Crystal Using a Quantum Cascade Laser," Applied Physics Letters, 101, 2012, 4 pages.
Sander, "Mid-Infrared Photothermal Imaging," Laser Science, Optical Society of America, 2015, p. LM1I.
Stolyarov et al., "Photothermal Speckle Modulation for Noncontact Materials Characterization," Opt. Lett., 40, 24, 2015, 5786-5789.
Winefordner et al., "Comparison of Calculated Detection Limits in Molecular Absorption, Molecular Luminescence, Raman, Molecular Ionization, and Photothermal Spectroscopy," Applied Spectroscopy, vol. 39, No. 3, 1985, 15 pages.
Application and file history of U.S. Appl. No. 16/877,152, filed May 18, 2020, Inventors: Li et al.
Application and file history of U.S. Appl. No. 16/427,866, filed May 31, 2019, Inventors: Decker et al.

\* cited by examiner

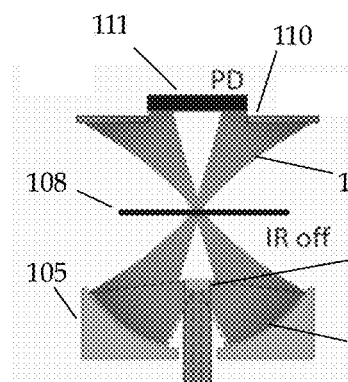
FIG. 1A
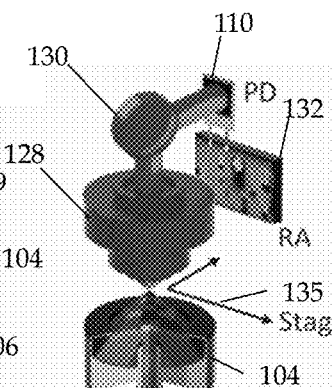
FIG. 1C
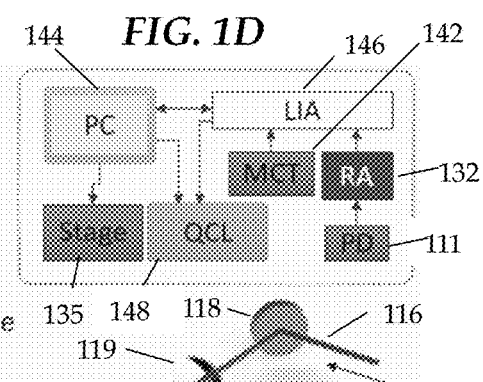
FIG. 1D
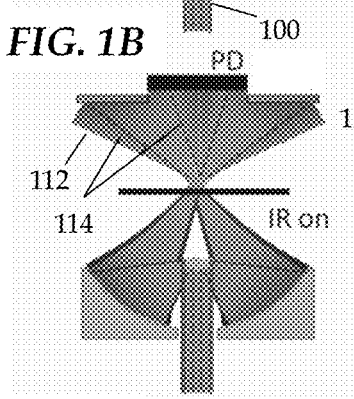
FIG. 1B
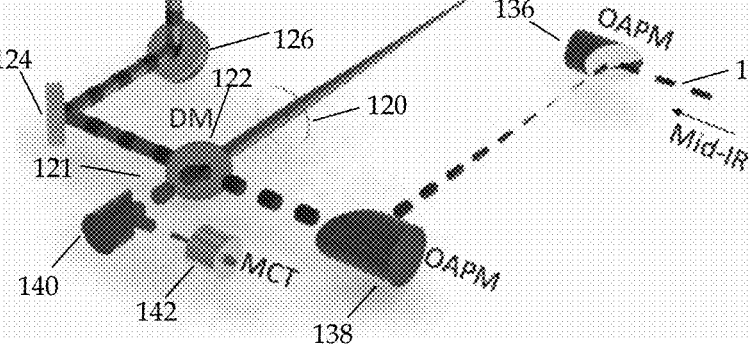
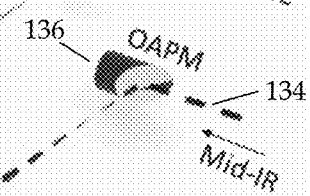

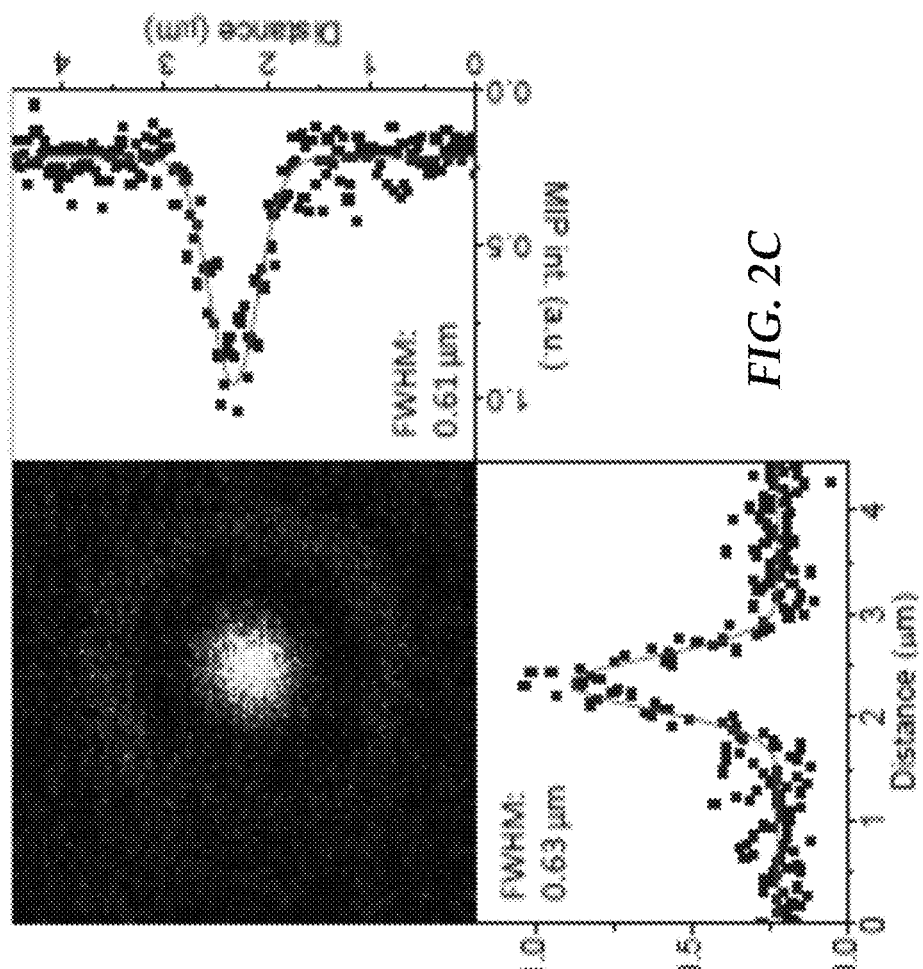
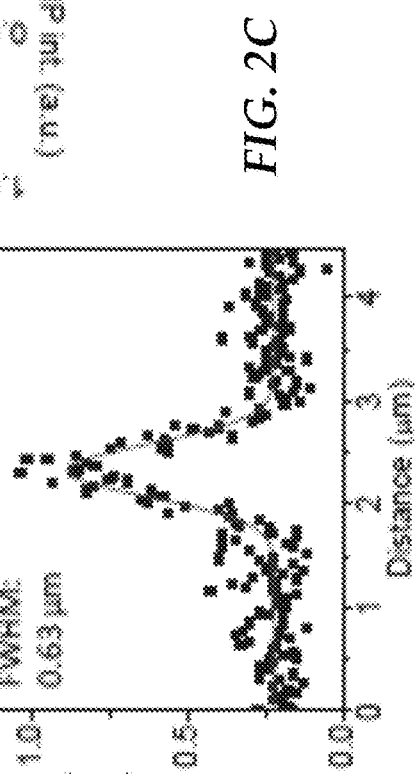
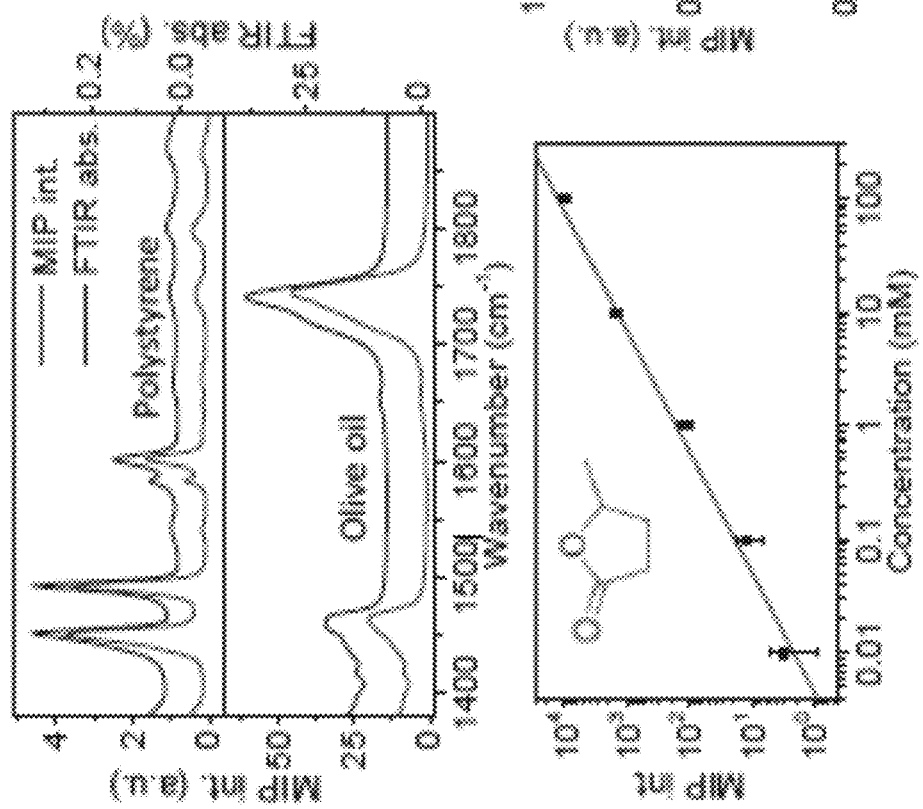
FIG. 2A
FIG. 2B
FIG. 2C

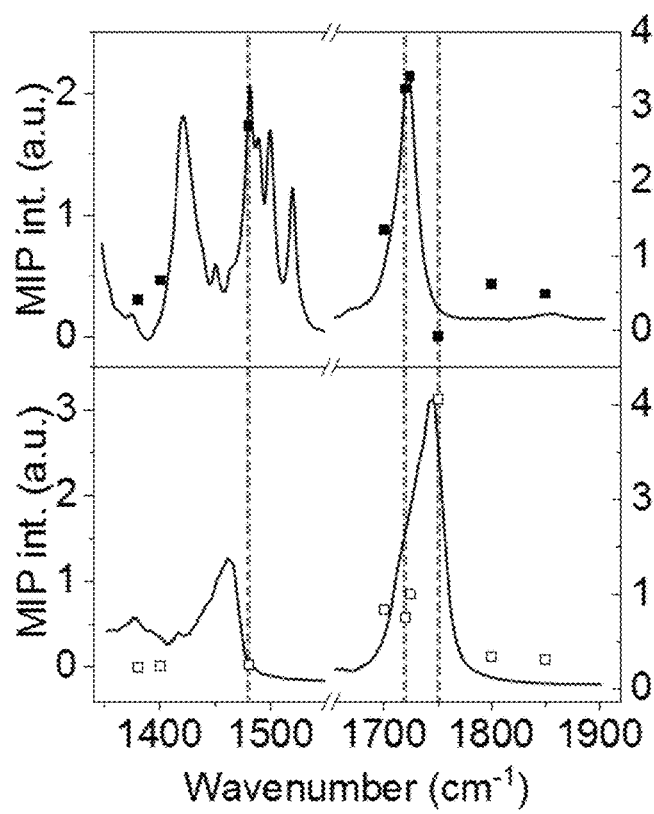
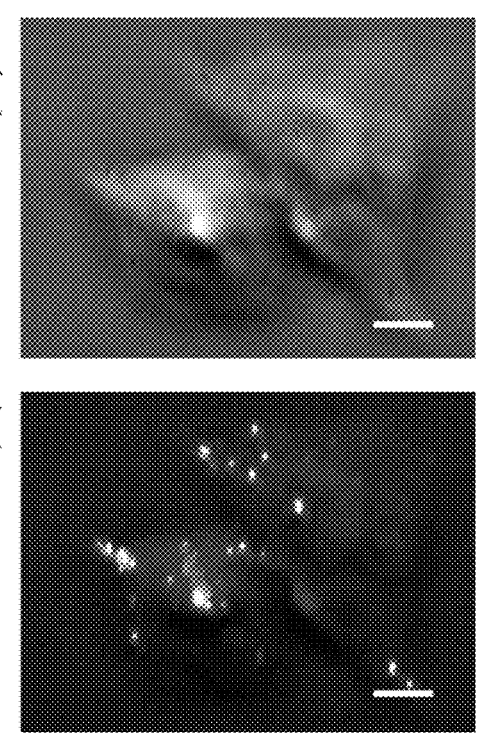
FIG. 4A
FIG. 4B
FIG. 4C

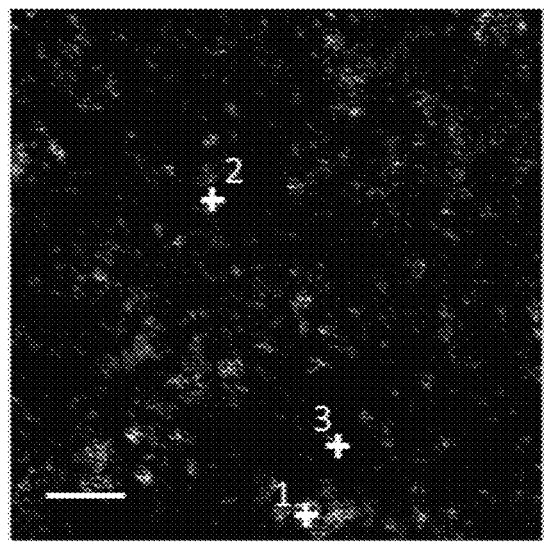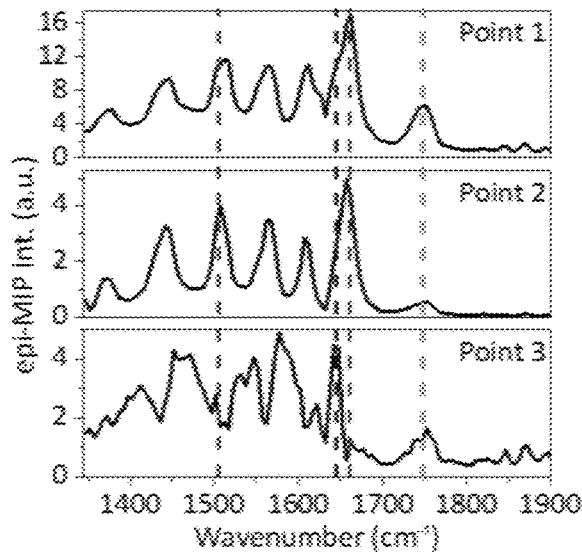
FIG. 8A                    FIG. 8B

DEPTH-RESOLVED MID-INFRARED PHOTOTHERMAL IMAGING OF LIVING CELLS AND ORGANISMS WITH SUB-MICRON SPATIAL RESOLUTION

RELATED APPLICATIONS

This application claims priority to U.S. Provisional Application, Ser. No. 62/400,582, filed Sep. 27, 2016, the contents of which are incorporated in their entirety

BACKGROUND

The specification relates to Mid-Infrared Photothermal (MIP) imaging and spectroscopy, and in particular MIP for acquiring information indicative of the optical properties and/or material composition of a surface that directly correlates to an infrared (IR) absorption spectrum. MIP may be a useful technique for measuring and mapping optical properties/material composition of some surfaces with resolution approaching nanometer scale.

SUMMARY

Devices and methods may be provided for sensing infrared absorption induced photothermal effects via a visible light source. A Mid-infrared photothermal probe (MI-PTP, or MIP) approach may achieve 10 mM detection sensitivity and sub-micron lateral spatial resolution. Such performance exceeds the diffraction limit of infrared microscopy and allows label-free three-dimensional chemical imaging of live cells and organisms. The MIP approach offers infrared absorption-based photo thermal effect imaging of molecules in living cells and C. elegans. The MIP approach has reached 10 uM detection sensitivity, sub-micron spatial resolution, and microsecond-scale pixel dwell times. Distributions of endogenous lipid and exogenous drug inside single cells can be visualized. MIP has also been used to demonstrate IR absorption imaging of lipids and proteins in C. elegans. MIP imaging technology may enable applications from monitoring metabolic activities to high-resolution mapping of drug molecules in living systems, which are beyond the reach of current infrared microscopy.

In a first aspect, a microscopic analysis system may be provided, including: a mid-IR optical source (MIR Source) that generates an infrared beam; an optical source that generates a probe beam; beam combining optics configured to combine the infrared and probe; an objective configured to focus the combined beams on to a sample; a detector to detect probe light from at least one of: probe light transmitted through the sample and probe light returning from the sample; and, a data acquisition and processing system for acquiring and processing detected probe light to generate a signal indicative of IR absorption by the sample, wherein the IR absorption signal has a spatial resolution of less than 1 micrometer.

In one embodiment of the first aspect, the imaging system may further include a focus translation stage to generate relative motion between the reflective objective and the sample to change the depth of focused spots of the IR and probe beams in the sample. In another embodiment of the first aspect, the signal indicative of IR absorption may be acquired at a plurality of points on the sample. In one embodiment of the first aspect, the signal indicative of IR absorption at the plurality of points may be used to generate an image indicative of IR absorption by the sample.

In another embodiment of the first aspect, the signal indicative of IR absorption at the plurality of points may be used to generate a chemical image of the sample. In one embodiment of the first aspect, the signal indicative of IR absorption may be measured at a plurality of wavelengths of the mid-IR source. In another embodiment of the first aspect, the signal indicative of IR absorption at a plurality of wavelengths may be indicative of an IR absorption spectrum of the sample. In one embodiment of the first aspect, IR absorption signals may be acquired at a plurality of positions of the focus stage to generate depth resolved maps of IR absorption of the sample.

In another embodiment of the first aspect, the depth resolved maps may have a spatial resolution in an axial direction of less than 4 micrometers. In one embodiment of the first aspect, the signal indicative of IR absorption may have a molecular concentration detection sensitivity of less than 10 millimolar. In another embodiment of the first aspect, the signal indicative of IR absorption may have a molecular concentration detection sensitivity of less than 1 millimolar. In one embodiment of the first aspect, the signal indicative of IR absorption may a molecular concentration detection sensitivity of less than 100 micromolar. In another embodiment of the first aspect, the signal indicative of IR absorption may have a molecular concentration detection sensitivity of less than 10 micromolar.

In one embodiment of the first aspect, the sample may be in liquid. In another embodiment of the first aspect, the sample may be a biological sample. In one embodiment of the first aspect, the biological sample may be living. In another embodiment of the first aspect, the signal indicative of IR absorption may be used to determine of at least one of: distribution of lipids, proteins, drug molecules, and metabolites.

In one embodiment of the first aspect, the electronic data acquisition and processing system may further include at least one resonant amplifier. In another embodiment of the first aspect, the electronics data acquisition and processing system may include at least one lock-in amplifier. In one embodiment of the first aspect, the measurement of IR absorption at a location on a sample may be acquired with a pixel dwell time of less than or equal to 500 microseconds.

In another embodiment of the first aspect, the mid-IR source may be a quantum cascade laser. In one embodiment of the first aspect, the mid-IR source may be a pulsed laser source. In another embodiment of the first aspect, the pulsed laser source may operate at a pulse rate of greater than or equal to 100 kHz.

In one embodiment of the first aspect, the spatial resolution may be 0.63 micrometers or better. In another embodiment of the first aspect, the imaging system may include a variable iris in an optical path between the sample at the detector to block at least a portion of probe light transmitted, reflected and/or scattered from the sample.

In one embodiment of the first aspect, the probe light detector may be configured to receive light from at least one of probe light transmission through the sample or probe light reflection from the sample surface. In another embodiment of the first aspect, the imaging system may include a monitoring detector configured to measure mid-IR beam power background in real time for normalization. In one embodiment of the first aspect, the objective may be a reflective objective. In another embodiment of the first aspect, the reflective objective may be at least one of a darkfield objective, a Schwarzschild objective or a Cassegrain objective.

In one embodiment of the first aspect, the probe beam optical source may be a visible laser. In another embodiment of the first aspect, the visible laser may be a CW laser diode source. In one embodiment of the first aspect, the probe beam optical source generates a beam within the wavelength range from visible to near-IR. In one embodiment of the first aspect, probe light may be deflected due to absorption of infrared light by the sample. In another embodiment of the first aspect probe light may be deflected due to a photothermal response of the sample resulting from absorption of infrared light by the sample.

In a second aspect, a microscopic analysis system may be provided, including: a mid-IR optical source (MIR Source) that generates an infrared beam; an optical source that generates a probe beam; beam combining optics configured to combine the infrared and probe beams; an objective configured to focus the combined beams on to a sample; a detector to detect at least one of: probe light transmitted through the sample and probe light returning from the sample; a focus stage to generate relative motion between the sample and the focus IR and probe beam spots to enable measurements of IR absorption at a plurality of locations on the sample, and; a data acquisition and processing system for acquiring and processing a signal indicative of IR absorption by the sample at the plurality of positions on the sample, wherein IR absorption signals may be acquired at a plurality of positions of the focus stage to generate depth resolved maps of IR absorption of the sample.

In one embodiment of the second aspect the depth resolved maps may have a spatial resolution in an axial direction of less than 4 micrometers.

In a third aspect, a microscopic analysis system may be provided, including: a mid-IR optical source (MIR Source) that generates an infrared beam; an optical source that generates a probe beam; beam combining optics configured to combine the infrared and probe; an objective configured to focus the combined beams on to a sample; a condenser to collect probe light transmitted through the sample; a detector to detect collected probe light; a data acquisition and processing system for acquiring and processing detected probe light to generate a signal indicative of IR absorption by the sample.

In a fourth aspect a method may be provided for imaging infrared absorption of a sample, the method including the steps of: illuminating a region of the sample with a beam of infrared (IR) radiation that is focused on the sample with an objective; illuminating at least a portion of the IR illuminated region with a probe light beam that is focused with the same objective as the IR beam; detecting at least a portion of probe light that is transmitted through or returning from the sample; and, analyzing variation in detected probe light to generate a signal indicative of IR absorption of the sample, wherein the IR absorption signal has a spatial resolution of less than 1 micrometer.

In one embodiment of the fourth aspect, the method may further include the step of generating relative motion between the reflective objective and the sample. In another embodiment of the fourth aspect, the method is repeated at a plurality of positions on the sample. In one embodiment of the fourth aspect, the method may further include generating an image indicative of IR absorption of the sample. In another embodiment of the fourth aspect, steps of the method are repeated at a plurality of wavelengths of the mid-IR beam and further comprising generating an IR absorption spectrum. In one embodiment of the fourth aspect, IR absorption spectra may be acquired at a plurality of positions of a focus translation stage to generate depth resolved maps of IR absorption spectra of the sample.

In another embodiment of the fourth aspect, the depth resolved maps have a spatial resolution in an axial direction of less than 4 micrometers. In one embodiment of the fourth aspect, images of IR absorption may be acquired at a plurality of positions of the focus translation stage to generate depth resolved maps of IR absorption of the sample. In another embodiment of the fourth aspect, the depth resolved maps may have a spatial resolution in an axial direction of less than 4 micrometers.

In one embodiment of the fourth aspect, the signal indicative of IR absorption may have a detection sensitivity of 10 millimolar or less. In another embodiment of the fourth aspect, the signal indicative of IR absorption may have a detection sensitivity of 1 millimolar or less. In one embodiment of the fourth aspect, the signal indicative of IR absorption may have a detection sensitivity of 100 micromolar or less. In another embodiment of the fourth aspect, the signal indicative of IR absorption may have a detection sensitivity of 10 micromolar or less.

In one embodiment of the fourth aspect, the sample may be in liquid. In another embodiment of the fourth aspect, the sample may be a biological sample. In one embodiment of the fourth aspect, the biological sample may be living. In another embodiment of the fourth aspect, the method may include the step of using the signal indicative of IR absorption to determine distribution of at least one of: lipids, proteins, drug molecules, and metabolites.

In one embodiment of the fourth aspect, the analyzing step may include using a resonant amplifier to amplify detected probe light. In another embodiment of the fourth aspect, the analyzing step may include using a lock-in amplifier to demodulate detected probe light. In one embodiment of the fourth aspect, the image of IR absorption may be acquired with a pixel dwell time of less than or equal to 500 microseconds.

In another embodiment of the fourth aspect, the beam of IR radiation may be emitted by a mid-IR source that comprises a pulsed laser source. In one embodiment of the fourth aspect, the lock-in amplifier may demodulate detected probe light at a frequency corresponding to a pulse repetition rate of the pulsed laser source. In another embodiment of the fourth aspect, the beam of IR radiation may be emitted by a mid-IR source that comprises a quantum cascade laser. In one embodiment of the fourth aspect, the pulsed laser source may operate at a pulse rate of greater than or equal to 100 kHz. In another embodiment of the fourth aspect, the spatial resolution may be 0.63 μm or better.

In one embodiment of the fourth aspect, the method may further include the step of transmitting probe light passing through the sample or returning from the sample through a variable iris thus blocking at least a portion of the probe light from reaching the detector. In another embodiment of the fourth aspect, the method may include detecting probe light from at least one of probe light transmission through the sample or probe light reflection from the sample surface. In one embodiment of the fourth aspect, the method may include the step of measuring the mid-IR beam power background in real time for normalization.

In another embodiment of the fourth aspect, the objective may be at least one of a darkfield objective, a Schwarzschild objective or a Cassegrain objective. In one embodiment of the fourth aspect, the method may include correlating the signal indicative of IR absorption to chemical species and identifying at least one chemical species present in the sample.

In another embodiment of the fourth aspect, the sample may be a pharmaceutical sample. In one embodiment of the fourth aspect, the signal indicative of IR absorption may be used to determine chemical species in the pharmaceutical sample. In another embodiment of the fourth aspect, the signal indicative of IR absorption may be measured at a plurality of locations on the sample to determine the distribution of at least one chemical species in the pharmaceutical sample.

In one embodiment of the fourth aspect, the sample may include at least one of a polymer or a mixture of polymers on an optional substrate. In another embodiment of the fourth aspect, the substrate may be made from at least one of the following materials: glass, silica, calcium fluoride, barium fluoride, magnesium fluoride, lithium fluoride, zinc sulfide, sapphire, IR polymer, zinc selenide, sodium chloride, potassium chloride, potassium bromide, thallium bromoiodide, and silicon. In one embodiment of the fourth aspect, the signal indicative of IR absorption may be used to determine chemical species of the sample. In another embodiment of the fourth aspect, the signal indicative of IR absorption may be measured at a plurality of locations on the sample to determine the distribution of at least one chemical species of the sample. In one embodiment of the fourth aspect probe light may be deflected due to absorption of infrared light by the sample. In another embodiment of the fourth aspect probe light may be deflected due to a photothermal response of the sample resulting from absorption of infrared light by the sample.

In a fifth aspect, a method may be provided for imaging infrared absorption of a sample, the method including the steps of: immersing at least a portion of the sample under liquid; illuminating a region of the sample with a beam of infrared (IR) radiation that is focused on the sample with an objective; illuminating at least a portion of the IR illuminated region with a probe light beam that is focused with the same objective as the IR beam; detecting at least a portion of probe light that is transmitted through or returning from the sample; and, analyzing variation in detected probe light to generate a signal indicative of IR absorption of the sample.

In one embodiment of the fifth aspect, the sample may be a biological sample. In one embodiment of the fifth aspect, the biological sample may be living. In another embodiment of the fifth aspect, the signal indicative of IR absorption may be used to determine at least one of: distribution of lipids, proteins, drug molecules, and metabolites. In one embodiment of the fifth aspect, the signal indicative of IR absorption may have a spatial resolution of less than 1 micrometer.

In another embodiment of the fifth aspect, the method may include the step of generate relative motion between the reflective objective and the sample to change the depth of focused spots of the IR and probe beams in the sample. In one embodiment of the fifth aspect, the method may include the step of generating depth resolved maps of IR absorption of the sample. In one embodiment of the fifth aspect probe light may be deflected due to absorption of infrared light by the sample. In another embodiment of the fifth aspect probe light may be deflected due to a photothermal response of the sample resulting from absorption of infrared light by the sample.

BRIEF DESCRIPTION OF THE DRAWINGS

Aspects and advantages of the embodiments provided herein are described with reference to the following detailed description in conjunction with the accompanying drawings.

Throughout the drawings, reference numbers may be re-used to indicate correspondence between referenced elements. The drawings are provided to illustrate example embodiments described herein and are not intended to limit the scope of the disclosure.

FIGS. 1A-1D show simplified schematic diagrams of an illustrative MIP embodiment including capability to perform measurements of IR absorption.

FIGS. 2A, 2B, and 2C show exemplary results achieved with an MIP system.

FIGS. 4A, 4B, and 4C show further exemplary results achieved with an MIP system.

FIGS. 8A and 8B show results of identifying chemical species using an MIP system operated in reflective or epi mode.

DETAILED DESCRIPTION OF ILLUSTRATIVE EMBODIMENT

Figure 3A:
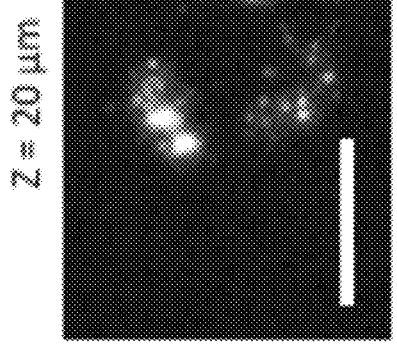
FIGS. 3A, 3B, 3C, 3D, 3E, and 3F show further exemplary results achieved with an MIP system.

Mid Infrared Photo-Thermal Probe (MIP) Imaging and Spectroscopy

The current disclosure is directed towards obtaining measurements of infrared optical properties of a material on a length scale much, much smaller than the diffraction limit of the infrared wavelengths employed, and in fact down to the sub-micron scale.

FIGS. 1A and 1B show simplified conceptual diagrams of a principle of high resolution photothermal detection of infrared absorption. Parallel beams of infrared light and a probe beam 100 are focused with the same reflective objective 105 onto a sample 108. The probe beam may be in the wavelength range from visible to near IR. In alternate embodiments the probe beam may have a wavelength in the ultraviolet. In general the probe beam wavelength is selected to be shorter than the mid-IR wavelengths such that the reflective objective will focus the probe beam to a smaller spot size than the mid-IR, thus enabling a higher spatial resolution measurement of IR absorption. In one embodiment the reflective objective can comprise a darkfield objective, or as shown in FIGS. 1A-1B, also referred to as a Schwarzchild or reverse Cassegrain objective. In this configuration, probe light and IR light are directed towards the central mirror 104 of reflective objective 105, which in turn direct the light to a second larger mirror 106 that focuses the light onto sample 108. Probe light beams 109 passing through the sample also pass through optional iris 110 and are detected by photodiode (PD) 111. FIG. 1A shows the situation when the IR light is off, for example in between pulses of IR light. FIG. 1B shows schematically how the probe beam propagation is perturbed by the addition of the infrared pump beam due to infrared absorption and development of a thermal lens. Absorption of IR light by the sample 108 causes the angular distribution of the probe beam to change. Conceptually, the undeflected probe beam is indicated by dashed lines 114, whereas the probe beam deflected by the thermal lensing is shown by shaded region 112. (This drawing is not to scale.) The formation of a thermal lens due to IR absorption of light by the sample 108 can lead to more or less light being detected by the photodiode (PD) 111.

FIG. 1C shows more detail of the Mid-IR Photothermal (MIP) system. Probe beam 116 is reflected off optional mirror 118. A pulsed mid-infrared pump beam 134 is provided by a quantum cascade laser (QCL, not shown) and a continuous probe beam 116 is provided by a visible laser (not shown), which are collinearly combined by a silicon dichroic mirror (DM, 122) and sent into a reflective objective lens 104 as described previously. The residual reflection 121 of the infrared beam from the dichroic mirror 122 is measured by a mercury cadmium-telluride (MCT) detector 142. The probe beam is collected by a condenser 128 with a variable iris (110 in FIG. 1A) and sent to a silicon photodiode (PD, 110) connected to an optional resonant amplifier (RA, 132). The condenser can be a commercial condenser, for example as used to focus illumination light in an optical microscope, or may be a microscope objective or other optical element to collect light transmitted through the sample and pass the light towards a detector. Other optional items are discussed below. The probe beam 116 can be expanded with a beam expander, for example made with lenses 119 and 120. Similarly, the IR beam 134 can be expanded with an IR beam expander, for example made with two off-axis parabolic mirrors (OAPM, 136 and 138). The beams may be directed, steered, and/or aligned using optional mirrors 118, 124, and 126. A stage indicated schematically by arrows 135 can provide sample translation to enable measurements at a plurality of locations on a sample, for example to create images of IR absorption by the sample.

Inset FIG. 1D shows a simplified schematic diagram of electronic and data components of the system. The photothermal signal measured by the photodiode (PD, 111) is optionally selectively amplified by the resonant amplifier (RA, 132) and optionally demodulated by a lock-in amplifier (LIA, 146). A computer (PC, 144) is used for control and data acquisition, including reading signals from lock-in amplifier 146, interfacing to the sample stage 135, and mid-IR source, e.g. a quantum cascade laser (QCL) 148.

FIGS. 2A, 2B and 2C show example spectral fidelity and spatial resolution performance achieved with an MI-PTP microscope. In FIG. 2A MIP spectral profiles and FTIR spectra (black) of polystyrene film (top) and olive oil (bottom) are shown. The FTIR spectra were acquired by an attenuated total reflection FTIR spectrometer. The spectra are offset for clarity. The MIP signal was normalized by the IR (using a QCL) power measured simultaneously via a same lock-in amplifier. The units for FTIR spectra are percent absorption, rather than the conventional absorbance, so that it is proportional to the infrared energy absorbed by the sample.

The sensitivity of MIP imaging was evaluated by measuring the 1775 $cm^{-1}$ C=O bond vibration of a small molecule, γ-valerolactone, in carbon disulfide solution (FIG. 2B). The limit of detection, or sensitivity, is found to be 10 µM with an infrared power of 2 mW and a probe power of 10 mW at the sample, when the standard deviation equals the solution-solvent difference. The time constant of the lock-in amplifier was set to 50 ms; and the spectral scan speed was set to 50 ms/$cm^{-1}$. Such sensitivity is beyond the reach of current Raman scattering based vibrational microscopes widely used for label-free imaging at intracellular level. As a comparison, the detection limit by stimulated Raman scattering microscopy was reported to be 200 µM for the strongest Raman band produced by C—C bond (32) achieved with 120 mW for pump and 130 mW for Stokes beam. For MIP imaging, we note that water absorption at the bending vibration weakens the infrared beam around 1645 $cm^{-1}$. Alternatively, deuterated water can be used to circumvent this difficulty. For ascorbic acid/D20, the detection sensitivity at the 1759 $cm^{-1}$ peak was found to be 6.7 mM under the same laser powers. To determine the spatial resolution of MIP, 500-nm Poly(methyl methacrylate) (PMMA) beads were imaged at the 1730 $cm^{-1}$ peak (FIG. 2C). The horizontal and vertical intensity profiles are plotted at the bottom and right side of the image. The measured full-width-at-half maximum (FWHM) was 0.63 µm in X and 0.61 µm in Y direction. In comparison, the diffraction limit of a 1730 $cm^{-1}$ infrared beam with the same NA 0.65 objective is 5.5 which is the theoretically best resolution achievable by an infrared microscope. The 9-fold improvement in resolution by MIP microscopy offers the opportunity of unveiling subcellular structures in living cells.

As illustrated, samples may include at least one of a polymer or a mixture of polymers on an optional substrate. The substrate may be made from at least one of the following materials: glass, silica, calcium fluoride, barium fluoride, magnesium fluoride, lithium fluoride, zinc sulfide, sapphire, IR polymer, zinc selenide, sodium chloride, potassium chloride, potassium bromide, thallium bromoiodide, and silicon.

As also illustrated, the signal indicative of IR absorption may be used to determine chemical species of the sample. Moreover, the signal indicative of IR absorption may be measured at a plurality of locations on the sample to determine the distribution of at least one chemical species of the sample.

Figure 3B:
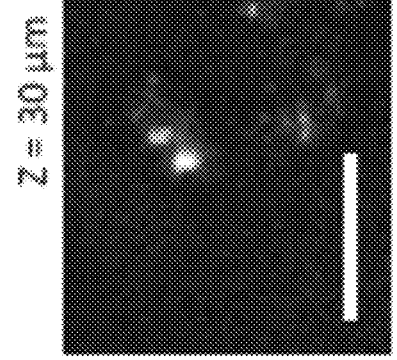
Figure 3C:
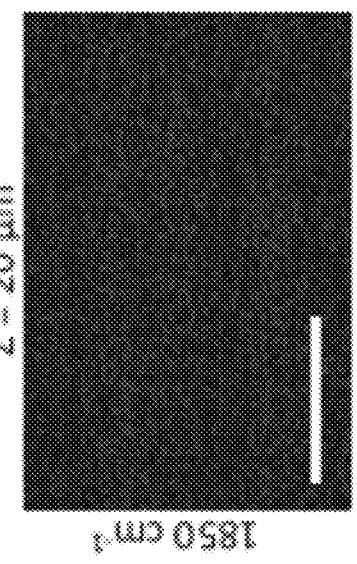
Figure 3D:
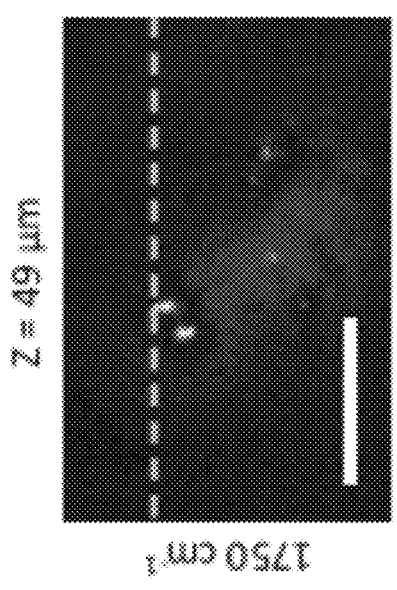
Figure 3E:
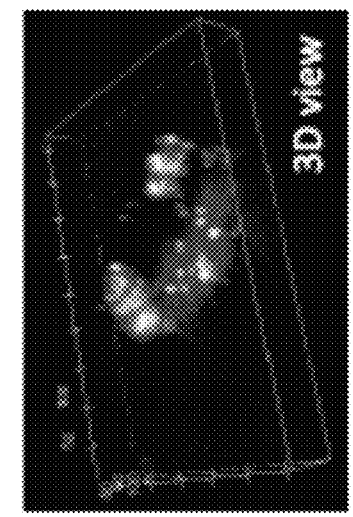
Figure 3F:
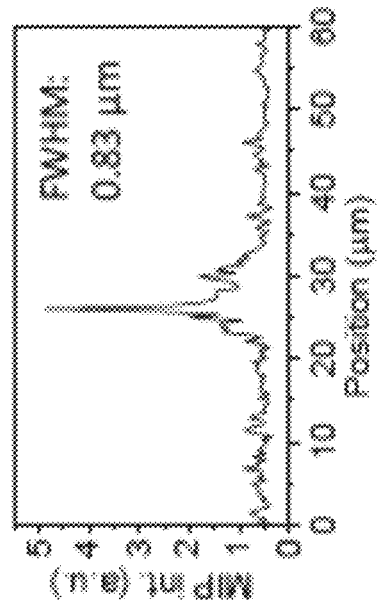

MIP imaging of lipids in live cells as shown in FIGS. 3A, 3B, and 3C illustrates example depth resolution achievable with an MIP imaging system. Depth-resolved MIP imaging of PC-3 cells at 1750 $cm^{-1}$ C=O band at difference Z positions is shown. In FIG. 3D the line profile indicated in FIG. 3A showing a FWHM of 0.83 µm of a small lipid droplet. In FIG. 3E the reconstructed 3D view of the same cell, showing individual lipid droplets over the cell body is shown. FIG. 3F shows off resonance image at 1850 $cm^{-1}$, showing no contrast. Pixel dwell time: 1 ms. Scale bars: 20 µm.

FIGS. 4A, 4B, and 4C show Multi-spectral MIP imaging of cellular drug uptake. FIG. 4A shows Infrared spectra of lipid inhibitor JZL184 (top, line) and olive oil (bottom, line). Squares are the multivariate curve resolution (MCR) results showing the spectral intensity for the drug and lipid content, respectively. Dashed lines indicate the characteristic peaks for drug and lipid. FIGS. 4B and 4C show MCR output of multi-spectral MIP imaging of JZL184 treated MIA PaCa-2 cells for drug (B) and lipid content (C). Pixel dwell time: 500 µs. Scale bars: 20 µm.

Figure 5A:
FIGS. 5A, 5B, 5C, 5D, and 5E show further exemplary results achieved with an MIP system.
Figure 5B:
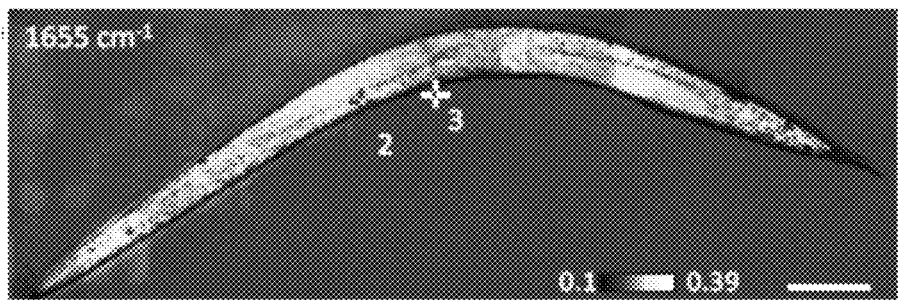
Figures 5C, 5D, 5E:
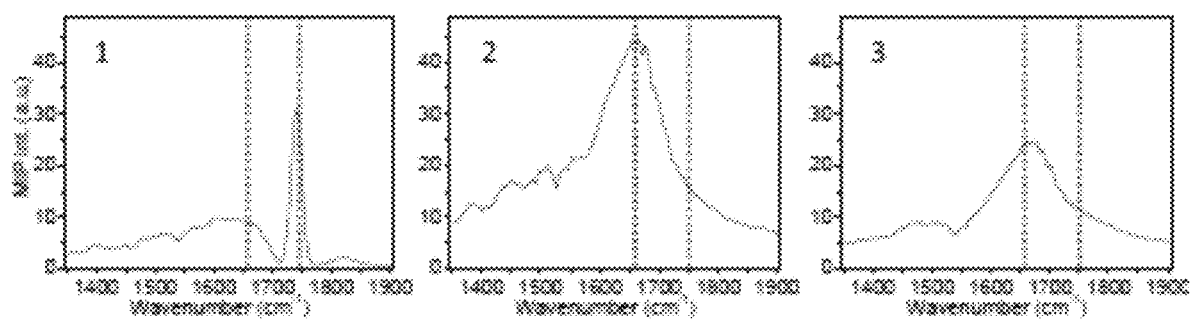

FIGS. 5A, 5B, 5C, 5D, and 5E show MIP imaging of lipid and protein in *Caenorhabditis elegans* (*C. elegans*). The figures demonstrate an unprecedented ability to make high resolution, chemical identification measurements on a live organism. FIG. 5A shows MIP imaging of the worm body at 1750 $cm^{-1}$ lipid C=O band. FIG. 5B shows MIP imaging of the same area at 1655 $cm^{-1}$ protein amide I band. FIGS. 5C, 5D, and 5E show pinpoint spectra of locations 1, 2, and 3, as indicated in FIGS. 4A and 4B. Blue and red lines indicate the wavelengths used in (a) and (b), respectively. Pixel dwell time: 500 µs. Scale bar: 200 µm.

Exemplary MI-PTP system elements are described below. Where appropriate callout numbers refer to FIGS. 1A-1D. A QCL 148 with 2 mW average power operating at 102 kHz pulse repetition rate (Block Engineering, LaserTune LT2000) tunable from 1345 $cm^{-1}$ to 1905 $cm^{-1}$, was expanded through a pair of off-axis parabolic mirrors (136 and 138) and combined collinearly with the probe laser, a continuous wave 785 nm laser (Thorlabs, LD785-SE400), by a silicon based dichroic mirror 122 (Edmund Optics, #68654). The combined beams were sent to an inverted microscope (Olympus, IX71). A reflective objective lens 104 (Edmund Optics, 52X NA 0.65, #66589) with gold coating was used for focusing. The samples 108 were mounted using calcium fluorite cover glasses in thickness of 0.5 mm or 1 mm. The probe laser was collected through a microscope condenser 128 with NA of 0.55 for forward detection by a silicon photodiode 110 (Hamamatsu, S3994-01). A scanning stage (Mad City Labs, Nano-Bio2200) was used for sample scanning at a maximum speed of 200 ms per pixel. The entire imaging system is purged by dry nitrogen to eliminate water vapor absorption.

The photocurrent from the silicon photodiode detector 111 was sent to a custom-built resonant amplifier 132, and then a lock-in amplifier 146 (Zurich Instruments, HF2LI) for phase sensitive detection to acquire the MIP signal. A fast mercury-cadmium-telluride (MCT) detector 142 (Vigo Inc., PVM-10.6) was used to monitor the QCL power through a second lock-in channel. A computer (PC 144) was used to: 1) control the tuning of QCL wavelength, 2) control the movement and read the real-time position of the piezo-stage 135 for sample scanning, and 3) collect spectroscopic data and reconstruct the images. A multichannel data acquisition card (National Instruments, PCIe-6363) was used for real-time data acquisition. Two calcium fluorite cover glasses (Eksma Optics, 530-6121) were used to sandwich two borosilicate capillary glass tube as inlet and outlet of the flow. The space was confined with additional No. 1 cover glasses with silicone based glue. The whole unit was put under the MIP microscope for sensitivity test with a flow rate about 1 mL/min using manual push. γ-valerolactone (Sigma Aldrich, W310301-1KG-K) was used as the analyte and dissolved into carbon disulfide. Concentrations of γ-valerolactone were determined by the volume used for preparation. The MIP intensities were calculated based on the 1775 cm$^{-1}$ peak area after subtraction of the solvent spectrum.

Improved spatial resolution was achieved using a high NA reflective objective with the input beam filling the input aperture of the objective. This was achieved using the two lenses 119 and 120 in FIG. 1 that form a beam expander. It was also used to adjust the divergence of the visible beam to maximize the MIP measurement sensitivity. For example this adjustment can ensure that the visible and IR have similar divergence, and focus at the same point in the vertical direction, and/or otherwise maximize the MIP signal strength.).

Several elements can also contribute to obtaining high spatial resolution in addition to the beam width engineering achieved with the steering/beam divergent optics and the objective. Using a pulsed MID-IR source such as a pulsed QCL leads to much narrower pulse widths compared to chopping mechanically a CW source. The short pulse times and high repetition rates can constrain thermal diffusion during sample heating, confining the heating effects to a smaller area. The optional use of a resonant amplifier, described elsewhere, enables low noise measurements at the desired high repetition rates.

A variable aperture or iris 110 can be configured to maximize the sensitivity of the MIP measurement. FIG. 1A schematically illustrates the probe light pattern during periods of no mid-IR excitation and FIG. 1B illustrates a change in the probe beam divergence that results from sample heating due to the absorption of IR light. The use of a variable aperture helps maximize the sensitivity of the MIP signal by creating an edge in the collection path where probe light beams are either passed to the detector or blocked depending on the thermal distortion of the sample. Adjusting the size of the iris can be used to maximize the sensitivity to the probe beam deviations, maximizing capture of the modified beam pattern produced during thermal excitation. This is shown in FIG. 1A for the non-thermally perturbed beam pattern compared to the thermally perturbed pattern of FIG. 1B.

Depth resolved measurements as obtained in FIGS. 3A. 3B, and 3D are obtainable with the MIP system for samples that are at least partially transparent to the probe beam wavelength(s). One way to obtain depth resolved images is to vary the focus depth using a focus translation stage that is part of the sample translation stage, alternatively an objective focus positioner could be employed. In either case, MIP measurements can be made where the focus point of the IR and probe beams are adjusted through a plurality of depths into the sample.

For spectrum measurements, an additional mid-IR detector such as a Mercury Cadmium Teluride (MCT) detector, measuring residual beam off of beam combiner, may be used to measure power background in real-time for normalization of spectra.

Figure 6A:
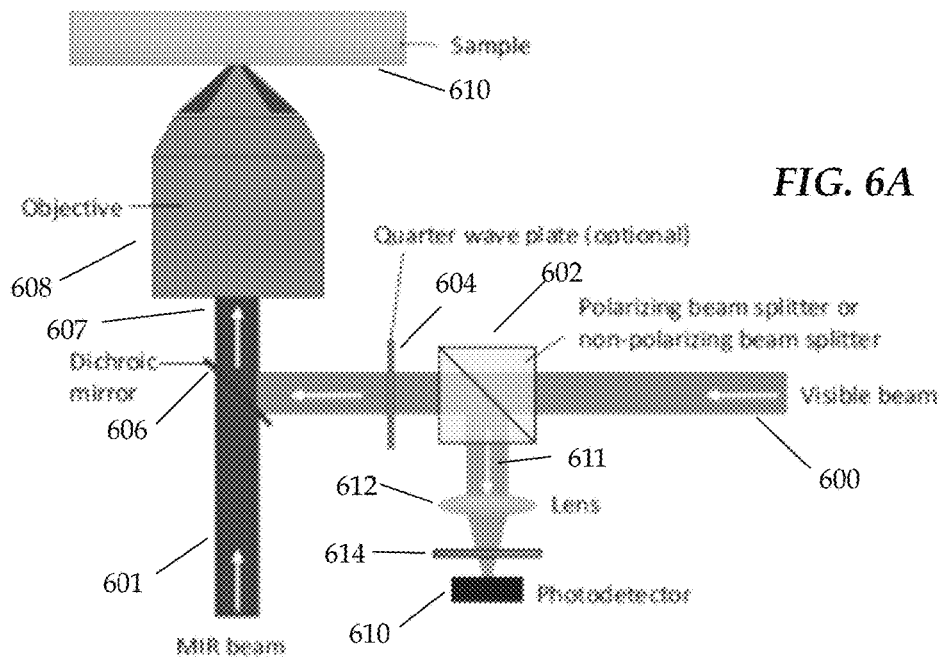
FIGS. 6A and 6B show simplified schematic diagrams of an embodiment of a MIP system operated in a reflective (epi) illumination/collection arrangement.
Figure 6B:
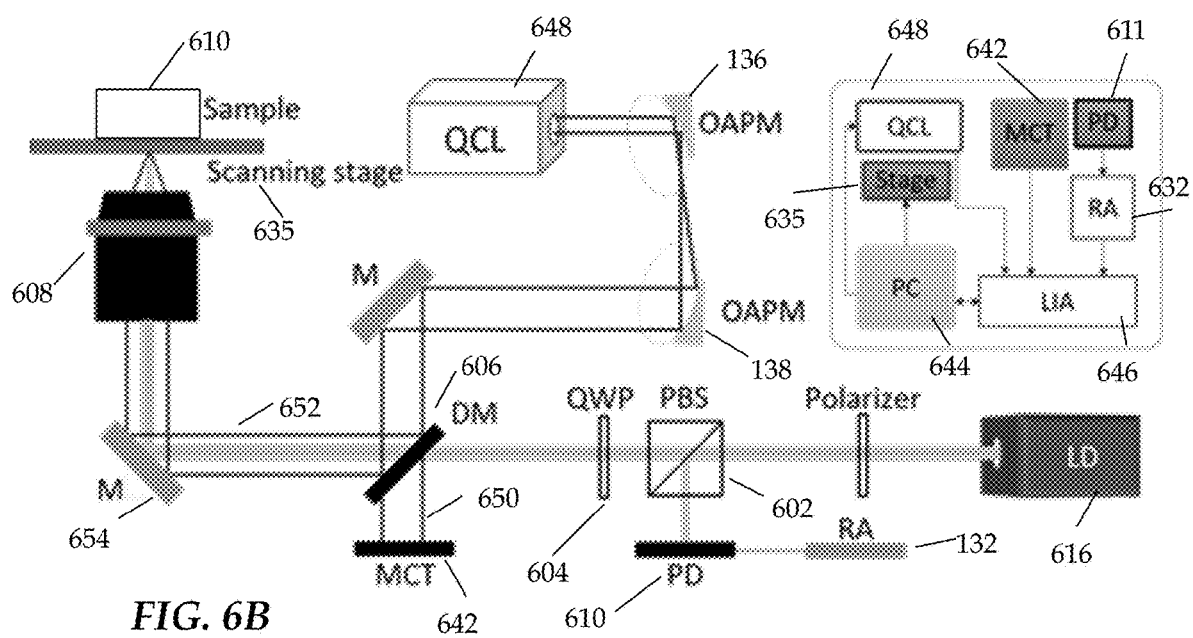

FIGS. 6A and 6B shows an embodiment of the current apparatus where the same objective 608 is used to illuminate the sample with IR and probe beams and collect the probe beam returning from the sample, i.e., reflected from the sample as opposed to transmitted through the sample as in the above embodiments. This "Epi-detected MIP microscope" embodiment works in the following way. Probe beam 600 and IR beam 601 are combined using a dichroic mirror 606, similarly to the descriptions associated with FIG. 1C above. A beamsplitter 602 is placed in the path of the probe beam 600 before the sample and advantageously before the beam combiner (e.g. dichroic mirror 606). The combined IR and probe beams 607 are focused with objective 608, for example a reflective objective as shown in FIG. 1, such that the IR and probe beams come to a focused spot on sample 610. Probe light that returns from the sample 610 may be collected by the same objective 608 as used to illuminate the sample. This reflective arrangement (also called "epi") eliminates the need that the sample be at least partially transparent to probe light as is required for the embodiment shown in FIG. 1. Probe light returning from the sample 610 through objective 608 is reflected off beam combiner/dichroic mirror 606, back to beamsplitter 602, where at least a portion of the probe light 611 is reflected towards a focusing element, e.g. lens 612 onto a photodetector 610. The beamsplitter 602 may be a polarizing beamsplitter or a non-polarizing beamsplitter. In the case of a polarizing beamsplitter, an optional quarter waveplate 604 can be used to generate elliptically polarized light that impinge on the sample such that light reflected from the sample and passing will be efficiently directed along an orthogonal path on the return trip, i.e. to the photodetector 610. Optional iris 614 can also be inserted into the beam path before the detector.

FIG. 6B shows a more detailed schematic of an embodiment of an epi-MIP microscope. A pulsed QCL source 648 provides the MIR beam and a continuous wave visible laser diode (LD, 616) is used as the probe beam. Both MIR and probe beams are combined by a silicon dichroic mirror (DM, 606), and the combined beams 652 are sent to optional mirror 654 and then sent into a reflective objective 608. The residue of the mid-IR light that is reflected from the dichroic mirror 606 may be optionally monitored by an IR detector, for example mercury cadmium telluride (MCT) detector 642. The backward propagated probe beam that is reflected/scattered from the sample is reflected by a polarizing beam splitter (PBS, 602) and sent to a silicon photodiode (PD, 610) connected optionally to a resonant amplifier (RA, 132). Inset: The epi-MIP signal is selectively amplified by the RA and sent into a lock-in amplifier (LIA, 646). The scanning stage 635, data acquisition and QCL tuning are controlled by a computer (PC, 644). Off axis parabolic mirrors (OAPM, 136 and 138) may optionally be used to expand the IR beam and/or to adjust the divergence of the IR beam to maximize the MIP signal strength. An optional polarizer or half wave plate may be used to adjust the incoming polarization of the probe beam to ensure maximum transmission through the polarizing beamsplitter, and/or to adjust the power of the probe beam. An optional quarter waveplate (QWP, 604) can be used to change linearly polarized light into elliptically polarized light. This polarization change is largely reversed on reflection such that a substantially fraction of light reflected from the sample is then directed on the alternate path in the polarizing beamsplitter (602) towards the photodiode 610. Alternately, a nonpolarizing beamsplitter can be used without the quarter waveplate. An optional beam expander (not shown, but for example similar to the one shown in FIG. 1) can also be used to expand the probe beam to an appropriate diameter to fill the back aperture of the reflective objective.

Figure 7A:
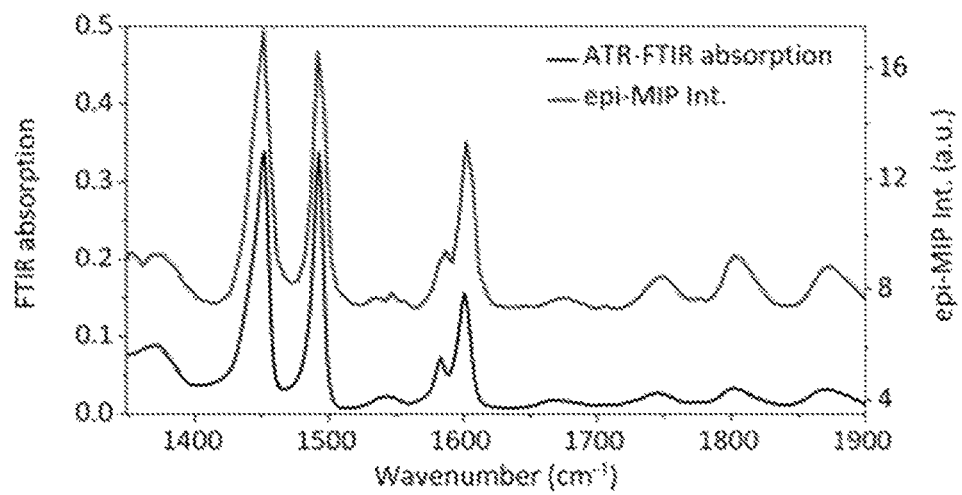
FIGS. 7A, 7B, and 7C show results characterizing the performance of an MIP system operated in reflective or epi mode.
Figure 7B:
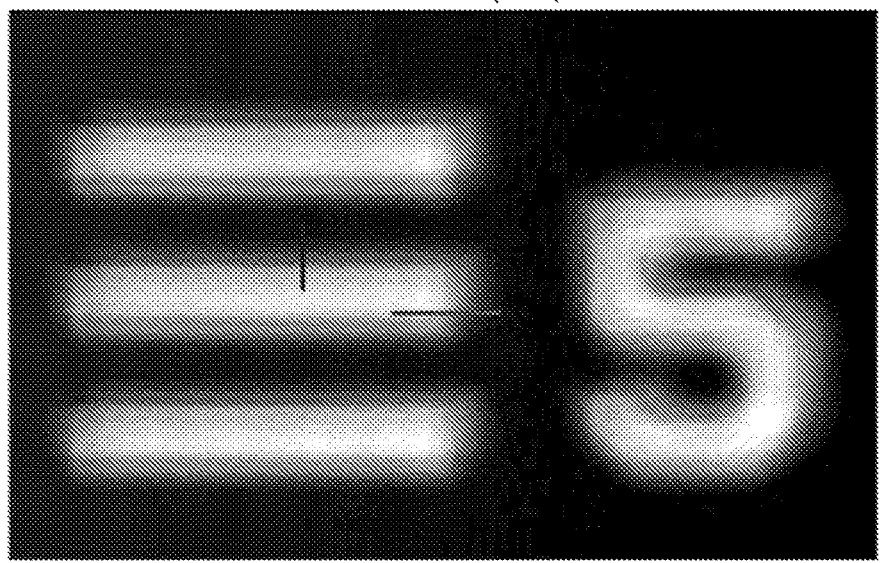
Figure 7C:
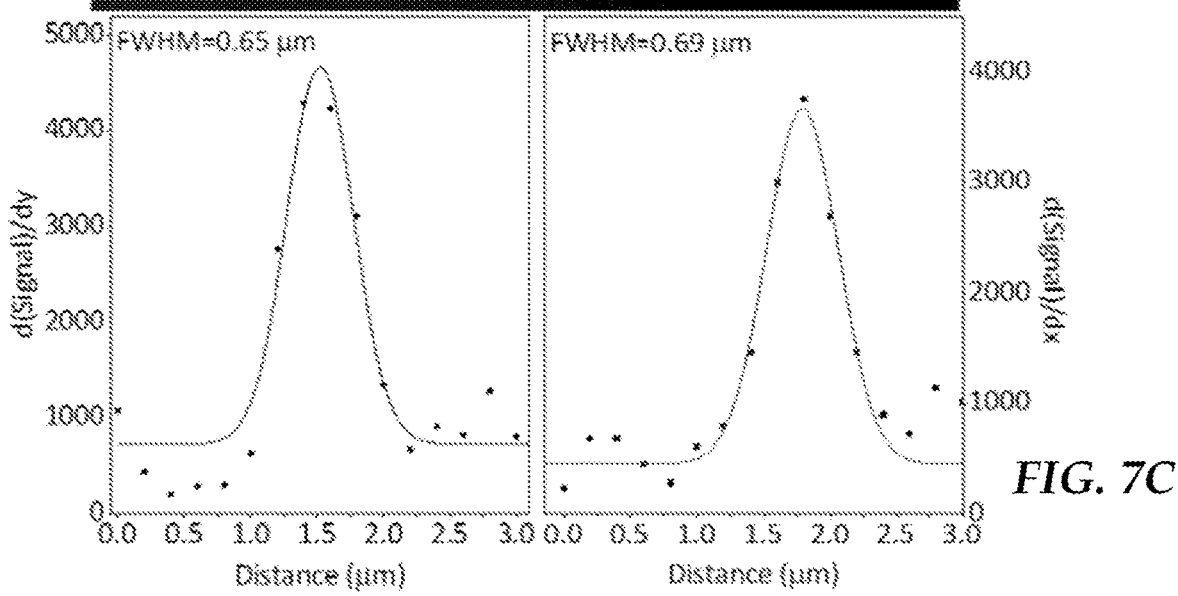

FIGS. 7A, 7B, and 7C illustrate characterization of epi-MIP microscope. In FIG. 7A comparison of epi-MIP IR absorption spectrum 700 with an FTIR spectrum 702 of a polystyrene film is shown. The spectra have been offset for clarity. The FTIR spectra were acquired by an attenuated total reflection FTIR spectrometer. The MIP signal was normalized by the QCL power measured simultaneously with the MCT detector 642 and via the same lock-in amplifier 646 as shown in FIG. 6B. In FIG. 7B epi-MIP image of the element 5 of group 5 on a positive 1951 USAF test target is shown. The 1st order derivative of the profiles of the horizontal and vertical lines are plotted in FIG. 7C. The measured FWHM is 0.69 µm and 0.65 µm respectively. Pixel dwell time: 1 ms. Scale bar is 20 µm.

In FIGS. 8A and 8B identification of different chemical species in a Tylenol tablet is shown. In FIG. 8A an epi-MIP image of tablet obtained at 1502 cm-1, corresponding to the benzene band of the active pharmaceutical ingredient (API) is shown. In FIG. 8B point spectra obtained with the epi-MIP device obtained of locations 1, 2 and 3, as indicated in FIG. 8A. Characteristic absorbance bands of different species are indicated with the dashed lines. The pixel dwell time was 500 µs. The scale bar for FIG. 8A is 50 µm.

The embodiments described herein are exemplary. Modifications, rearrangements, substitute processes, alternative elements, etc. may be made to these embodiments and still be encompassed within the teachings set forth herein. One or more of the steps, processes, or methods described herein may be carried out by one or more processing and/or digital devices, suitably programmed.

Depending on the embodiment, certain acts, events, or functions of any of the method steps described herein can be performed in a different sequence, can be added, merged, or left out altogether (e.g., not all described acts or events are necessary for the practice of the algorithm). Moreover, in certain embodiments, acts or events can be performed concurrently, rather than sequentially.

The various illustrative logical blocks, optical and control elements, and method steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a processor configured with specific instructions, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration.

The elements of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of computer-readable storage medium known in the art. An exemplary storage medium can be coupled to the processor such that the processor can read information from, and write information to, the storage medium. In the alternative, the storage medium can be integral to the processor. The processor and the storage medium can reside in an ASIC. A software module can comprise computer-executable instructions which cause a hardware processor to execute the computer-executable instructions.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X, Y or Z, or any combination thereof (e.g., X, Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to illustrative embodiments, it will be understood that various omissions, substitutions, and changes in the form and details of the devices or methods illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

We claim:

1. A system for microscopic analysis of a sample, comprising:
    a mid-IR optical source that generates an infrared beam;
    an optical source that generates a probe beam;
    beam combining optics configured to combine the infrared beam and the probe beam as combined beams;
    an objective stage configured to focus the combined beams on to the sample;
    a detector to detect probe light from at least one of: the probe beam transmitted through the sample and the probe beam returning from the sample; and
    a data acquisition and processing system configured to acquire and process the probe light from the detector to generate a signal indicative of IR absorption by the sample, wherein the signal indicative of IR absorption has a spatial resolution of less than 1 micrometer,
    wherein the sample is in liquid.

2. The system of claim 1 wherein the signal indicative of IR absorption has a molecular concentration detection sensitivity of less than 10 millimolar.

3. The system of claim 1 wherein the signal indicative of IR absorption has a molecular concentration detection sensitivity of less than 1 millimolar.

4. The system of claim 1 wherein the signal indicative of IR absorption has a molecular concentration detection sensitivity of less than 100 micromolar.

5. The system of claim 1 wherein the signal indicative of IR absorption has a molecular concentration detection sensitivity of less than 10 micromolar.

6. The system of claim 1 wherein the sample is a biological sample.

7. The system of claim 6 wherein the biological sample is living.

8. The system of claim 6 wherein the signal indicative of IR absorption is used to determine of at least one of a distribution of: lipids, proteins, drug molecules, and metabolites.

9. The system of claim 1 wherein the signal indicative of IR absorption at the location on the sample are acquired with a pixel dwell time of less than or equal to 500 microseconds.

10. The system of claim 1 wherein the mid-IR optical source comprises an electronically pulsed laser source.

11. The system of claim 10 wherein the pulsed laser source operates at a pulse rate of greater than or equal to 100 kHz.

12. The system of claim 1 wherein the spatial resolution is 0.63 micrometers or better.

13. The system of claim 1 further comprising a variable iris in an optical path between the sample and the detector to block at least a portion of probe light that is transmitted, reflected and/or scattered from the sample.

14. The system of claim 1 wherein at least a portion of probe light is deflected due to absorption of infrared light by the sample.

15. A method for imaging infrared absorption of a sample, the method comprising:
    immersing at least a portion of the sample under liquid;
    illuminating a region of the sample with a beam of infrared (IR) radiation that is focused on the sample with an objective;
    illuminating at least a portion of the IR illuminated region with a probe light beam that is focused with the same objective as the IR beam;
    detecting at least a portion of probe light that is transmitted through or returning from the sample;
    analyzing variation in detected probe light to generate a signal indicative of IR absorption of the sample.

16. The method of claim 15 further comprising correlating the signal indicative of IR absorption to chemical species and identifying at least one chemical species present in the sample.

17. The method of claim 15 wherein the sample is a pharmaceutical sample.

18. The method of claim 17 wherein the signal indicative of IR absorption is used to determine chemical species in the pharmaceutical sample.

19. The method of claim 17 wherein the signal indicative of IR absorption is measured at a plurality of locations on the sample to determine the distribution of at least one chemical species in the pharmaceutical sample.

20. The method of claim 15 wherein the sample is a biological sample.

21. The method of claim 20 wherein the biological sample is living.

22. The method of claim 15 wherein the signal indicative of IR absorption is used to determine of at least one of: distribution of lipids, proteins, drug molecules, and metabolites.

23. The method of claim 22 wherein the substrate is made from at least one of the following materials: glass, silica, calcium fluoride, barium fluoride, magnesium fluoride, lithium fluoride, zinc sulfide, sapphire, IR polymer, zinc selenide, sodium chloride, potassium chloride, potassium bromide, thallium bromoiodide, and silicon.

24. The method of claim 22 wherein the signal indicative of IR absorption is used to determine chemical species of the sample.

25. The method of claim 22 wherein the signal indicative of IR absorption is measured at a plurality of locations on the sample to determine the distribution of at least one chemical species of the sample.

26. The method of claim 15 wherein the signal indicative of IR absorption has a spatial resolution of less than 1 micrometer.

27. The method of claim 15 further comprising the step of generate relative motion between the reflective objective and the sample to change the depth of focused spots of the IR and probe beams in the sample.

28. The method of claim 27 further comprising the step of generating depth resolved maps of IR absorption of the sample.

29. The method of claim 15 wherein the sample is comprised of at least one of a polymer or a mixture of polymers on an optional substrate.

30. The method of claim 15 wherein probe light is deflected due to absorption of infrared light by the sample.

31. The method of claim 15 wherein probe light is deflected due to a photothermal response of the sample resulting from absorption of infrared light by the sample.

* * * * *